(12) United States Patent
Konrad et al.

(10) Patent No.: US 6,589,995 B2
(45) Date of Patent: Jul. 8, 2003

(54) METHOD OF INHIBITING PANCREATIC β-CELL P135 O-GLYCOSYLATION

(75) Inventors: Robert Konrad, Carmel, IN (US); Jeffrey Kudlow, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/813,534

(22) Filed: Mar. 21, 2001

(65) Prior Publication Data

US 2002/0128235 A1 Sep. 12, 2002

Related U.S. Application Data

(60) Provisional application No. 60/190,785, filed on Mar. 21, 2000.

(51) Int. Cl.⁷ .......................... A01N 33/24; A61K 31/13
(52) U.S. Cl. .......................... 514/644; 514/645; 514/335
(58) Field of Search ................. 514/644, 645, 514/335; 435/325

(56) References Cited

U.S. PATENT DOCUMENTS 6,361,995 B1 * 3/2002 Konrad et al. ............... 435/325
6,391,895 B1 * 5/2002 Towart et al. ............... 514/335

OTHER PUBLICATIONS

Haendeler et al., "Effects of redox–related congeners of NO on apoptosis and caspase–3 activity", Nitric Oxide, 1997, (4) 282–93, Medline Abstract, AN: 1998368273.*

* cited by examiner

Primary Examiner—Zohreh Fay
Assistant Examiner—Brian-Yong Kwon
(74) Attorney, Agent, or Firm—Benjamin Aaron Adler

(57) ABSTRACT

The present invention demonstrates a method for inhibiting O-linked protein glycosylation in a tissue or cell, comprising the step of contacting said tissue or cell with (Z)-1-[N-(3-Ammoniopropyl)-N-(n-propyl)amino] diazen-ium-1,2-diolate or a derivative thereof. The present invention is also directed to a method of treating or inhibiting the onset of diabetes mellitis in an individual in need of such treatment, comprising the step of admininstering to said individual a pharmacological dose of a compound which inhibiting O-linked protein glycosylation in a tissue or cell of said individual. Further, the present invention provides a pharmaceutical composition, comprising (Z)-1-[N-(3-Ammoniopropyl)-N-(n-propyl)amino] diazen-ium-1,2-diolate and a pharmaceutically acceptable carrier or a derivative thereof.

1 Claim, 3 Drawing Sheets

NOC-15

DPTA

Spermine NONOate

N-Acetylglucosamine (GlcNAc)

NOC-15

METHOD OF INHIBITING PANCREATIC β-CELL P135 O-GLYCOSYLATION

CROSS-REFERENCE TO RELATED APPLICATION

This non-provisional patent application claims benefit of provisional patent application U.S. Serial No. 60/190,785 filed Mar. 21, 2000, now abandoned.

FEDERAL FUNDING LEGEND

This invention was produced in part using funds obtained through grant number DK55262 from the National Institutes of Health. Consequently, the federal government has certain rights in this invention.

BACKGROUND OF THE INVENTION

1. Field of the Invention

The present invention relates generally to the field of medical therapy for diabetes. More specifically, the present invention relates to a new method for preventing and/or treating diabetes.

2. Description of the Related Art

Early in the course of type 2 diabetes, pancreatic β-cell function is sufficient such that in many patients, oral hypoglycemic agents are adequate for the treatment of the disease. As type 2 diabetes progresses, however, high blood glucose (sugar) concentrations appear to lead to the loss of capacity of the β-cells in the pancreatic islets to produce sufficient amounts of insulin to control the blood glucose. Thus, a vicious cycle arises wherein high blood glucose destroys β-cell function leading to even higher blood glucose and worsening of the condition. The mechanism by which glucose may be toxic to β-cells, however, has remained unknown.

Recent data suggests that glucose shares an important property with streptozotocin (STZ), a diabetogenic toxin that has been used for the past several decades to create animal models of diabetes (1). It has been shown that both high levels of glucose and streptozotocin stimulate O-linked glycosylation of a 135 kD protein present in pancreatic islets called p135 (2). Increased O-glycosylation of p135 causes beta-cell death. This suggests a mechanism for how the high levels of glucose present in the pre-diabetic (or early diabetic) state may cause full-blown diabetes to develop.

The prior art is deficient in the lack of effective means of blocking p135 O-glycosylation specifically, or the O-glycosylation of any other proteins generally. The prior art is also deficient in the lack of an effective means for preventing and/or treating diabetes. The present invention fulfills these long-standing needs and desires in the art.

SUMMARY OF THE INVENTION

The present invention is based on the fact that both glucose and the diabetogenic compound streptozotocin stimulate p135 O-glycosylation in pancreatic islets (2). The present invention shows that it is possible to pharmacologically block this process of O-glycosylation from occurring. The present invention in addition demonstrates the basic molecular structure on an inhibitor of such O-linked protein glycosylation.

In one embodiment of the present invention, there is provided a new method for inhibiting the process of O-linked protein glycosylation wherein the compound (Z)-1-[N-(3-Ammoniopropyl)-N-(n-propyl)amino] diazen-ium-1,2-diolate (Also known as PAPA NONOate or NOC-15) is used to inhibit O-glycosylation.

In another embodiment of the present invention, there is provided a new method for inhibiting p135 O-linked protein glycosylation wherein the compound (Z)-1-[N-(3-Ammoniopropyl)-N-(n-propyl)amino] diazen-ium-1,2-diolate (Also known as PAPA NONOate or NOC-15) is used to inhibit pancreatic beta-cell O-glycosylation.

In another embodiment of the present invention, there is provided a new method for inhibiting streptozotocin-induced pancreatic beta-cell p135 O-linked protein glycosylation wherein the compound (Z)-1-[N-(3-Ammoniopropyl)-N-(n-propyl)amino] diazen-ium-1,2-diolate (Also known as PAPA NONOate or NOC-15) is used.

In another embodiment of the present invention, the molecular structure of the compound (Z)-1-[N-(3-Ammoniopropyl)-N-(n-propyl)amino] diazen-ium-1,2-diolate (Also known as PAPA NONOate or NOC-15) is provided and is shown to be an analog of N-acetylglucosamine, when the latter is drawn in its linear form.

In another embodiment of the present invention, the molecular structure of the compound (Z)-1-[N-(3-Ammoniopropyl)-N-(n-propyl)amino] diazen-ium-1,2-diolate (Also known as PAPA NONOate or NOC-15) is provided and compared to the structures of similar compounds that do not inhibit O-glycosylation, indicating what structural aspects are necessary for inhibition of protein O-glycosylation.

In another embodiment of the present invention, the concept of using NOC-15, NOC-15-related molecules, other structural analogs of N-acetylglucosamine, or other related molecules to inhibit O-linked protein glycosylation is proposed, with the idea that such inhibition will be useful in the prevention and/or treatment of diabetes.

In another embodiment of the present invention, the concept of using NOC-15, NOC-15-related molecules, other structural analogs of N-acetylglucosamine, or other related molecules to inhibit the pancreatic beta-cell enzyme O-linked N-acetylglucosamine transferase (OGT) is proposed, with the idea that such inhibition will be useful in the prevention and/or treatment of diabetes.

In another embodiment of the present invention, the concept of using NOC-15, NOC-15-related molecules, other structural analogs of N-acetylglucosamine, or other related molecules to inhibit O-linked protein glycosylation in tissues other than pancreatic beta-cells is proposed, with the idea that O-glycosylation may be an important pathway in other disease processes and that inhibition of this pathway may be of great clinical utility.

In another embodiment of the present invention, the concept of using NOC-15, NOC-15-related molecules, other structural analogs of N-acetylglucosamine, or other related molecules to inhibit O-linked N-acetylglucosamine transferase (OGT) in tissues other than pancreatic beta-cells is proposed, with the idea that O-glycosylation may be an important pathway in other disease processes and that inhibition of this pathway may be of great clinical utility.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Streptozotocin (STZ), an analog of N-acetylglucosamine (GlcNAc), is a specific toxin for the pancreatic β-cell (1–3). Streptozotocin has been demonstrated to act by inhibiting the enzyme O-GlcNAcase, which cleaves O-linked N-acetylglucosamine off protein (3). When administered to rats or other animals, streptozotocin causes diabetes. Treatment of rats with streptozotocin also results in vivo in an early β-cell-specific increase in the level of intracellular protein modification by O-linked N-acetylglucosamine (O-GlcNAc) (3). Treatment of isolated islets with streptozotocin in vitro results in increased O-glycosylation of a protein called p135 (1). High levels of glucose also have the same effect on p135 (1).

Since streptozotocin causes diabetes and glucose shares with streptozotocin the effect of increased p135 O-glycosylation, it is very likely that the way in which diabetes occurs is that high levels of glucose present early in the course of pre-diabetes are toxic to pancreatic beta-cells in the same manner as streptozotocin. This leads to beta-cell failure, which leads to higher levels of glucose, which leads to more beta-cell failure, etc. Eventually, enough beta-cells are damaged/destroyed that full blown diabetes develops. Therefore, in order to prevent and/or treat diabetes, it is necessary to inhibit pancreatic beta-cell O-linked protein glycosylation.

Figure 1:
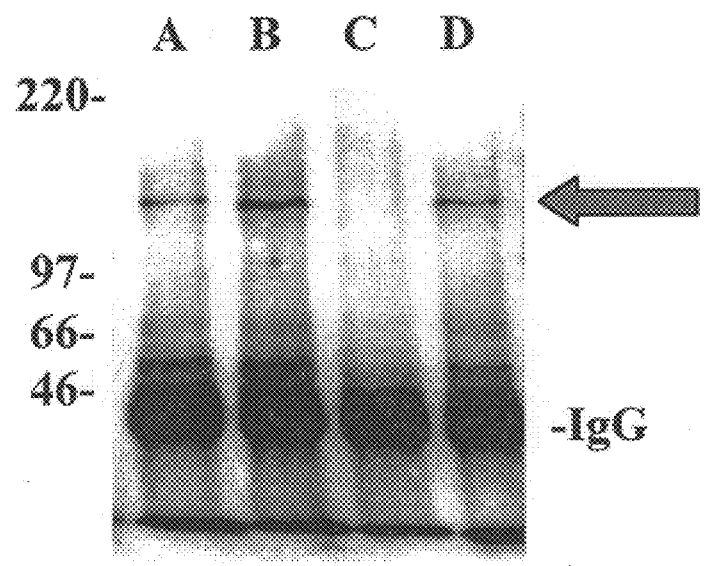
FIG. 1 shows what occurs if islets are stimulated with 3 mM glucose (lane A), 5 mM streptozotocin (lane B), 5 mM NOC-15 (lane C) or 5 mM DPTA (lane D). After immunoprecipitation and Western blotting of O-glycosylated protein with RL2 antibody, p135 is shown to undergo increased O-glycosylation in response to streptozotocin. DPTA has no effect on p135 O-glycosylation compared to 3 mM glucose. In contrast, NOC-15 completely abolishes p135 O-glycosylation.
Figure 2:
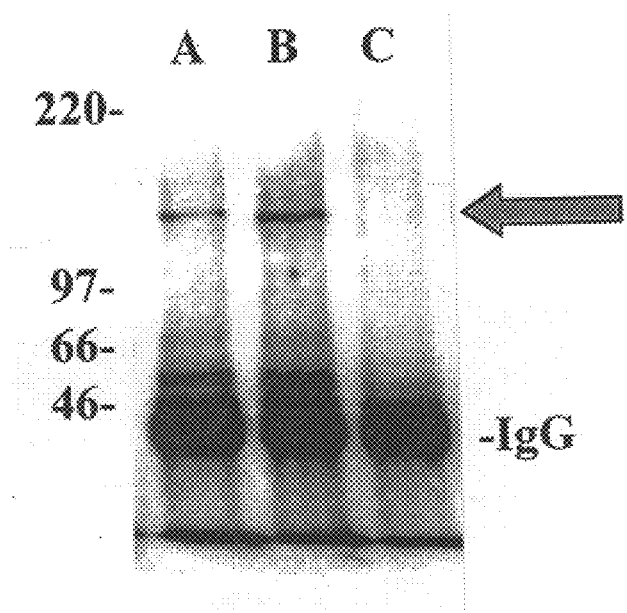
FIG. 2 shows what occurs if islets are stimulated with 3 mM glucose (lane A), 5 mM streptozotocin (lane B), or 5 mM streptozotocin and 5 mM NOC-15 (lane C). After immunoprecipitation and Western blotting of O-glycosylated protein with RL2 antibody, p135 is shown to undergo increased O-glycosylation in response to streptozotocin. The addition of NOC15, even in the presence of streptozotocin is able to almost completely abolish p135 O-glycosylation.

This can be accomplished by using the drug NOC-15, which is a structural analog of N-acetylglucosamine, the natural substrate of O-linked N-acetylglucosamine transferase (4–8). As can clearly be seen from FIGS. 1 and 2, NOC-15 is able to inhibit pancreatic beta-cell p135 O-glycosylation, even when islets are treated with 5 mM streptozotocin. The ability of NOC-15 to counteract even the effect of 5 mM streptozotocin suggests that almost complete inhibition of O-glycosylation is possible. This data thus suggests a possible pharmacologic approach to preventing or treating diabetes.

NOC-15 is a nitric oxide donor and thus probably acts by binding to O-linked N-acetylglucosamine transferase and giving off at least one (and possibly 2) molecule(s) of nitric oxide in the active site of the enzyme, thus inactivating O-linked N-acetylglucosamine transferase and abolishing the process of O-linked protein glycosylation. Obviously, because it acts as a nitric oxide donor, NOC-15 may not be optimally suitable for human use. However, by modifying its basic structure, a person having ordinary skill in this art would be able to synthesize an inhibitor of O-linked N-acetylglucosamine transferase that does not have the undesirable side effect of acting as a nitric oxide donor.

Figure 3:
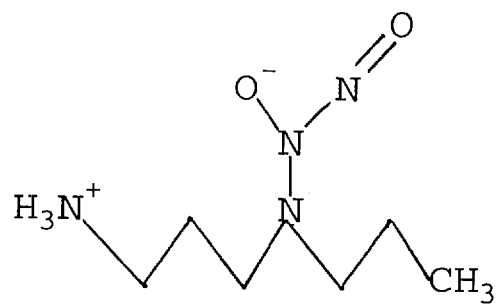
FIG. 3 shows the molecular structures of NOC-15, and the similar molecules DPTA, and Spermine NONOate. In contrast to NOC-15, DPTA and Spermine NONOate do not inhibit p135 O-glycosylation, indicating that the terminal methyl group present in NOC-15 may be critical for its ability to inhibit O-glycosylation.
Figure 3:
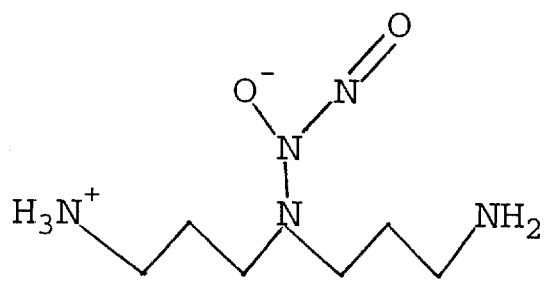
Figure 3:
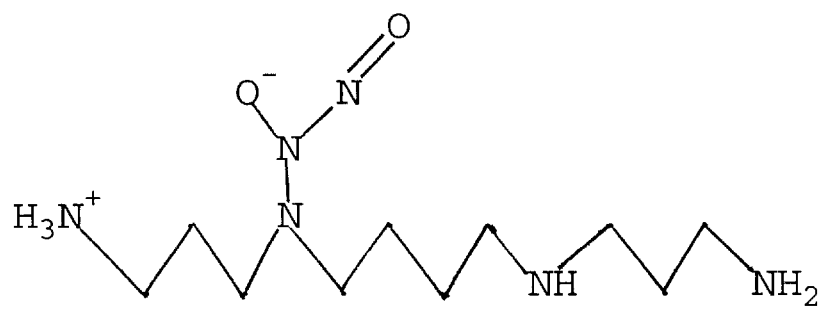

FIG. 3 also shows that the methyl group present at the end of the side chain is essential for NOC-15's activity. The related molecules DPTA NONOate and Spermine NONOate, which differ only slightly in structure with respect to this methyl group, do not have the ability to inhibit O-linked protein glycosylation. Thus, by using the information contained herein, it would be possible to synthesize a non-toxic inhibitor of O-linked protein glycosylation and such an inhibitor should prove extremely useful in preventing and/or treating diabetes mellitus.

In one embodiment of the present invention, there is provided a new method for inhibiting the process of O-linked protein glycosylation wherein the compound (Z)-1-[N-(3-Ammoniopropyl)-N-(n-propyl)amino] diazen-ium-1,2-diolate (Also known as PAPA NONOate or NOC-15) is used to inhibit O-glycosylation.

In another embodiment of the present invention, there is provided a new method for inhibiting p135 O-linked protein glycosylation wherein the compound (Z)-1-[N-(3-Ammoniopropyl)-N-(n-propyl)amino] diazen-ium-1,2-diolate (Also known as PAPA NONOate or NOC-15) is used to inhibit pancreatic beta-cell O-glycosylation.

In another embodiment of the present invention, there is provided a new method for inhibiting streptozotocin-induced pancreatic beta-cell p135 O-linked protein glycosylation wherein the compound (Z)-1-[N-(3-Ammoniopropyl)-N-(n-propyl)amino] diazen-ium-1,2-diolate (Also known as PAPA NONOate or NOC-15) is used.

In another embodiment of the present invention, the molecular structure of the compound (Z)-1-[N-(3-Ammoniopropyl)-N-(n-propyl)amino] diazen-ium-1,2-diolate (Also known as PAPA NONOate or NOC-15) is provided and is shown to be an analog of N-acetylglucosamine, when the latter is drawn in its linear form.

In another embodiment of the present invention, the molecular structure of the compound (Z)-1-[N-(3-Ammoniopropyl)-N-(n-propyl)amino] diazen-ium-1,2-diolate (Also known as PAPA NONOate or NOC-15) is provided and compared to the structures of similar compounds that do not inhibit O-glycosylation, indicating what structural aspects are necessary for inhibition of protein O-glycosylation.

In another embodiment of the present invention, the concept of using NOC-15, NOC-15-related molecules, other structural analogs of N-acetylglucosamine, or other related molecules to inhibit O-linked protein glycosylation is proposed, with the idea that such inhibition will be useful in the prevention and/or treatment of diabetes.

In another embodiment of the present invention, the concept of using NOC-15, NOC-15-related molecules, other structural analogs of N-acetylglucosamine, or other related molecules to inhibit the pancreatic beta-cell enzyme O-linked N-acetylglucosamine transferase (OGT) is proposed, with the idea that such inhibition will be useful in the prevention and/or treatment of diabetes.

In another embodiment of the present invention, the concept of using NOC-15, NOC-15-related molecules, other structural analogs of N-acetylglucosamine, or other related molecules to inhibit O-linked protein glycosylation in tissues other than pancreatic beta-cells is proposed, with the idea that O-glycosylation may be an important pathway in other disease processes and that inhibition of this pathway may be of great clinical utility.

In another embodiment of the present invention, the concept of using NOC-15, NOC-15-related molecules, other structural analogs of N-acetylglucosamine, or other related molecules to inhibit O-linked N-acetylglucosamine transferase (OGT) in tissues other than pancreatic beta-cells is proposed, with the idea that O-glycosylation may be an important pathway in other disease processes and that inhibition of this pathway may be of great clinical utility.

EXAMPLE 1

NOC-15 Inhibits Pancreatic Islet p135 O-glycosylation

Rat pancreatic islets were isolated as previously described (1). After isolation, islets were counted into tubes and pre-incubated with 3 mM glucose. Following pre-incubation, islets were stimulated with 3 mM glucose, 5 mM streptozotocin, 5 mM NOC-15, or 5 mM DPTA. At the end of the experiment, O-glycosylated proteins were immunoprecipitated with RL2 antibody, which binds to O-linked N-acetylglucosamine (3). Immunoprecipitated proteins were run out on a 6.5% SDS-PAGE gel and the proteins were then transferred to a nitrocellulose blot. The blot was then probed with RL2 antibody, which was detected by the ECL method. The blot was exposed to X-ray film and the film was developed and photographed.

The results shown demonstrate that islets contain a major O-glycosylated protein called p135 and that its O-glycosylation is stimulated by streptozotocin. DPTA has no effect on p135 O-glycosylation, but NOC-15 completely abolishes it.

NOC-15 Inhibits STZ-Induced Pancreatic Islet p135 O-glycosylation

Rat pancreatic islets were isolated as in example 1. After isolation, islets were counted into tubes and pre-incubated with 3 mM glucose. Following pre-incubation, islets were stimulated with 3 mM glucose, 5 mM glucose, or the combination of 5 mM streptozotocin and 5 mM streptozotocin. At the end of the experiment, islet O-glycosylated proteins were immunoprecipitated with RL2 antibody, which binds to O-linked N-acetylglucosamine (3). Immunoprecipitated proteins were run out on a 6.5% SDS-PAGE gel and the proteins were transferred to a nitrocellulose blot. The blot was probed with RL2 antibody, which was detected by the ECL method. The blot was exposed to X-ray film, and the film was developed and photographed. The results shown indicate that NOC-15 is capable of almost completely inhibiting streptozotocin-induced p135 O-glycosylation. These data suggest that the pancreatic beta-cell O-glycosylation pathway (which is involved in the development of streptozotocin-induced diabetes) is amenable to pharmacologic therapy. The structure and action of NOC-15 can thus be used as a basis to synthesize drugs that can be used to prevent and/or treat diabetes.

Discussion

Streptozotocin (STZ), an analog of N-acetylglucosamine (GlcNAc), is a specific toxin for the pancreatic β-cell. Streptozotocin has been demonstrated to act by inhibiting the enzyme O-GlcNAcase, which cleaves O-linked N-acetylglucosamine off protein (3). When administered to rats or other animals, streptozotocin causes diabetes. Treatment of rats with streptozotocin also results in vivo in an early β-cell-specific increase in the level of intracellular protein modification by O-linked N-acetylglucosamine (O-GlcNAc) (3). Treatment of isolated islets with streptozotocin in vitro results in increased O-glycosylation of a protein called p135 (1). High levels of glucose also have the same effect on p135 (1). The pancreatic beta-cell is likely exquisitely sensitive to streptozotocin because it contains 100–1000 fold more of the enzyme O-linked N-acetylglucosamine transferase (OGT) than any other cell type.

The fact that glucose shares with streptozotocin the ability to increase p135 O-glycosylation suggests a way in which high levels of glucose present early in the course of diabetes are toxic to pancreatic beta-cells in the same manner as streptozotocin. This glucose toxicity thus leads to beta-cell failure, which leads to higher levels of glucose, which leads to more beta-cell failure, etc. Eventually, enough beta-cells are damaged/destroyed that full-blown diabetes develops. Therefore, in order to prevent and/or treat diabetes, it is necessary to inhibit pancreatic beta-cell O-linked protein glycosylation and/or p135 O-glycosylation.

This can be accomplished with the drug NOC-15. As can clearly be seen from FIGS. 1 and 2, NOC-15 is able to inhibit pancreatic beta-cell p135 O-glycosylation, even when islets are treated with 5 mM streptozotocin. The ability of NOC-15 to counteract even the effect of streptozotocin suggests that almost complete inhibition of pancreatic beta-cell O-glycosylation is possible. These data suggest a possible pharmacologic approach to preventing or treating diabetes. These data also represent the first description of any kind of pharmacologic inhibition of the process of O-linked protein glycosylation.

Figure 4:
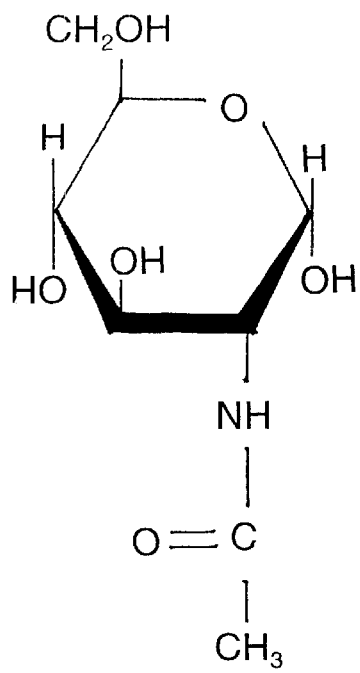
FIG. 4 shows the molecular structures of NOC-15, and N-Acetylglucosamine (GlcNAc). It is apparent from the structures that NOC-15 is an analog of N-Acetylglucosamine.
Figure 4:
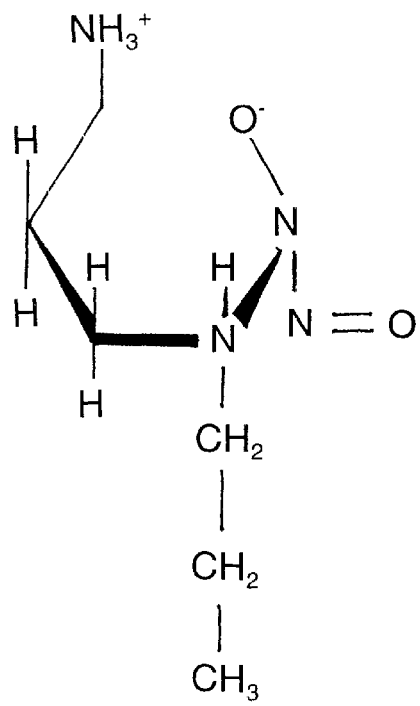

As can be seen in FIG. 3, NOC-15 is a nitric oxide donor. It can also be seen from FIG. 4 that NOC-15 is an analogue of N-acetylglucosamine, the natural substrate of O-linked N-Acetylglucosamine transferase (OGT). NOC-15 thus probably acts by binding to O-linked N-Acetylglucosamine transferase and giving off at least one molecule of nitric oxide in the active site of the enzyme, thus inactivating the enzyme and abolishing the process of O-linked protein glycosylation. It is possible (although less likely) that NOC-15 inhibits one of the other enzymes involved in the process of O-linked protein glycosylation. Because it acts as a nitric oxide donor, NOC-15 is probably not optimally suitable for human use. However, by modifying its basic structure, it should be possible to synthesize a competitive inhibitor of O-glycosylation that does not have the undesirable side effect of acting as a nitric oxide donor.

FIG. 3 also shows that the methyl group present at the end of the side chain is essential for NOC-15's activity, since the related molecules DPTA and Spermine NONOate, which differ only slightly in structure with respect to this side chain, do not inhibit O-linked protein glycosylation. Thus, by using the information contained in this patent, it should be possible to synthesize a non-toxic inhibitor of O-linked protein glycosylation and such an inhibitor should prove extremely useful in preventing and/or treating diabetes mellitus.

In addition, the process of O-linked protein glycosylation may be involved in many other disease processes. This disclosure contains the first description of any kind of how to pharmacologically inhibit protein O-glycosylation. As a result, targeted drug design based on these observations may lead to O-glycosylation inhibitors that are useful for treating many other important diseases.

Thus, the present invention is directed to a method for inhibiting O-linked protein glycosylation in a tissue or cell, comprising the step of contacting said tissue or cell with (Z)-1-[N-(3-Ammoniopropyl)-N-(n-propyl)amino] diazen-ium-1,2-diolate or a derivative thereof. In a preferred embodiment, the tissue is pancreatic beta-cells. In a preferred embodiment, the O-linked protein glycosylation is p135 O-linked protein glycosylation. In one aspect, the derivative of (Z)-1-[N-(3-Ammoniopropyl)-N-(n-propyl)amino] diazen-ium-1,2-diolate is a structural analog of N-acetylglucosamine. The inhibition of pancreatic beta-cell O-linked protein glycosylation is useful in the prevention and/or treatment of diabetes. Preferably, the (Z)-1-[N-(3-Ammoniopropyl)-N-(n-propyl)amino] diazen-ium-1,2-diolate or derivative thereof inhibits pancreatic beta-cell O-linked N-acetylglucosamine transferase.

The present invention is also directed to a method of treating or inhibiting the onset of diabetes mellitus in an individual in need of such treatment, comprising the step of admininstering to said individual a pharmacological dose of a compound which inhibiting O-linked protein glycosylation in a tissue or cell of said individual. Generally, the compound would inhibit O-linked protein glycosylation in pancreatic beta-cells. For example, the compound preferably inhibits p135 O-linked protein glycosylation. A representative example of a compound that inhibits p135 O-linked protein glycosylation is Z)-1-[N-(3-Ammoniopropyl)-N-(n-propyl)amino] diazen-ium-1,2-diolate or a derivative thereof. A derivative of (Z)-1-[N-(3-Ammoniopropyl)-N-(n-propyl)amino] diazen-ium-1,2-diolate could be a structural analog of N-acetylglucosamine.

The present invention is also directed to a pharmaceutical composition, comprising (Z)-1-[N-(3-Ammoniopropyl)-N-(n-propyl)amino] diazen-ium-1,2-diolate and a pharmaceutically acceptable carrier or a derivative thereof.

The present invention is also directed to a method of inhibiting the onset of diabetes mellitus or treating diabetes mellitus in an individual in need of such treatment, comprising the step of: admininstering to said individual a pharmacological dose of a pharmaceutical composition of the present invention.

The following references were cited herein.

Konrad, R. J, et al., *Biochem. Biophys. Res. Comm.* 267:26–32, 2000

Heff, R. R., et al., *J. Amer. Chem. Soc.* 89:4808–4809, 1967

Roos M. D., et al, *Proc. Assoc. Amer. Physicians.* 110: 1–11, 1998

Kornfeld, R., *J. Biol. Chem.,* 242:3135–3141, 1967

McKnight, G. L., et al., *J. Biol. Chem.,* 267:25208–25212, 1992

Sayeski, P. P., et al., *J. Biol. Chem.* 271:15237–15243, 1996

Kreppel, L. K., et al., *J. Biol. Chem.* 272:9308–9315, 1997

Lubas, W. A., et al., *J. Biol. Chem.* 272:9316–9324, 1997

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for inhibiting p135 O-linked protein glycosylation in a tissue or cell, comprising the step of contacting said tissue or cell with (Z)-1-[N-(3-Ammoniopropyl)-N-(n-propyl)amino] diazen-ium-1,2-diolate or a derivative thereof, wherein said tissue is pancreatic beta-cells.

* * * * *